United States Patent [19]
Flanagan et al.

[11] Patent Number: 4,812,120
[45] Date of Patent: Mar. 14, 1989

[54] IMPLANTABLE PERCUTANEOUS DEVICE

[76] Inventors: Dennis F. Flanagan, 129 Summit Rd., Storrs, Conn. 06268; Stephen H. Clark, 347 Cooper La., Coventry, Conn. 06238

[21] Appl. No.: 115,401

[22] Filed: Nov. 2, 1987

[51] Int. Cl.⁴ ............................................. A61C 8/00
[52] U.S. Cl. .................................. 433/173; 433/176; 433/201.1
[58] Field of Search ............... 433/173, 174, 175, 176, 433/201.1; 623/16

[56] References Cited

U.S. PATENT DOCUMENTS

| | | | |
|---|---|---|---|
| 3,683,422 | 8/1972 | Stemmer et al. | 623/16 |
| 3,745,590 | 7/1973 | Stubstad | 623/16 |
| 3,934,347 | 1/1976 | Lash et al. | 433/180 |
| 4,270,905 | 6/1981 | Mohammed | 433/201.1 |

FOREIGN PATENT DOCUMENTS

| | | | |
|---|---|---|---|
| 0024008 | 2/1981 | European Pat. Off. | 433/173 |
| 2455828 | 8/1976 | Fed. Rep. of Germany | 433/176 |

*Primary Examiner*—John J. Wilson
*Attorney, Agent, or Firm*—Ira S. Dorman

[57] ABSTRACT

A prosthetic dental device, adapted for percutaneous implantation, consists of a metal core that is directly coated with a first layer of polymer, and is overcoated with a second polymeric layer in which fibrils of a biopolymer are embedded and secured. The fibril nap provides a framework for the growth and attachment of regenerating recipient connective tissue, and also serves as a barrier against epithelial invasion, which would otherwise tend to cause implant rejection.

20 Claims, 1 Drawing Sheet

IMPLANTABLE PERCUTANEOUS DEVICE

BACKGROUND OF THE INVENTION

Numerous applications exist for percutaneous implants, serving as medical and dental prostheses. A fundamental concern associated with the implantation of such devices arises from the natural tendency for the immune system of the host human or other mammal to reject such foreign objects. This occurs primarily through epithelial invasion mechanisms, although the formation of scar tissue, and cellular migration and proliferation around implants, have also contributed to the failure of efforts to develop permanent prostheses.

Exemplary of the prior art that is germane to this technology are the following United States patents:

Mizuguchi et al U.S. Pat. No. 3,556,969 discloses a method in which collagen fibrils are electrodeposited from an aqueous suspension, to produce a shaped article in which the fibrils are randomly arranged.

In accordance with Tregear et al U.S. Pat. No. 3,700,609 a polymer, such as polyethylene or polypropylene, is grafted with an aromatic monomer containing a protein-reactive group to achieve improved compatibility with mammalian body tissue. The resultant structure may be used as a prosthesis to which protein bonding is promoted.

A process for coating synthetic polymers with collagen is described in Okamura et al U.S. Pat. No. 3,808,113, in which a spark plug discharge is used for surface preparation, followed by irradiation of the collagen coating. It is disclosed that medical articles produced exhibit an affinity to living bodies, as well as having other desirable properties.

Pillet U.S. Pat. No. 3,863,344 provides an implantable support for a dental prosthesis, which may be comprised of a stainless steel pin surrounded by a resilient envelope of an organosilicic elastomer. A textile sheet may be adhesively affixed to the surface of the envelope, to render it colonizable by living tissue.

Seiderman U.S. Pat. No. 4,034,750 discloses a bandage adapted for topical application, comprised of a semipermeable collagen membrane which may be linked electrochemically to damaged collagen fibrils of an animal body.

Yannis et al U.S. Pat. No. 4,060,081 provides a membrane including, as one layer, a cross-linked composite of collagen and a mucopolysaccharide and, as a second layer, a silicon resin, an acrylate or methacrylate ester polymer or copolymer, or polyurethane; a reactive prepolymer may be employed to produce the laminate. Subcutaneous implantation, collagen fibrosynthesis at the graft/host tissue interface, and multilayer systems are disclosed, the latter using a silicon elastomer for bonding the composite layer to another material.

Morris U.S. Pat. No. 4,307,472 teaches a technique for increasing the bond strength between a porous polymeric coating, used on a surgical implantation device to accommodate and promote tissue ingrowth, and the underlying structural component, the surface of which may be roughened or otherwise prepared by providing grooves or the like upon it. An interfacial layer is provided between the underlying structural component and the porous coating; for example, nonporous polyethylene may be used for the substrate when porous polyethylene is employed as the outer layer.

A composite polymeric material, consisting of a methacrylic or acrylic ester polymer or copolymer and fibrillar collagen, is provided by Stole et al U.S. Pat. No. 4,427,808. The polymeric material may be applied to a solid support, or it may be reinforced with metallic materials.

Park U.S. Pat. No. 4,491,987 discloses a prosthesis comprised of a metal alloy body, the surface of which may be etched with acid and coated with a methylmethacrylate polymer or copolymer, for improved bonding with bone cement.

DIALOG Information Services, Inc. has published the abstract of an application in the name of Kantrowitz et al, claiming a U.S. priority date of May 31, 1984 and Ser. No. 615,883, which concerns a device to be implanted below the skin and to project outwardly for assembly with a detachable member. The surface of the device is covered with a cultured autologous multilayer fibroblast coating, and the device is implanted in a surgically formed pocket. An advantage disclosed is that epidermal downgrowth along the side of the device is blocked to prevent rejection.

In addition to the patent art, the function of a stable collagen/biomaterial seal in inhibiting epidermal downgrowth is hypothesized in *Contemporary Biomaterials* (Noyes Publications, Park Ridge, N.J. 1984), beginning at page 506.

Despite the activity in the art indicated by the foregoing references, a demand remains for an implantable percutaneous device for dental use, which is highly effective in providing a support for a dental prosthesis and in avoiding immunological rejection due to epithelial invasion. Accordingly, it is the broad object of the present invention to provide a novel device affording such features and advantages.

It is a related object of the invention to provide a novel method by which such an implantable percutaneous device can be produced, and also to provide a novel method of surgical implantation utilizing such a device.

SUMMARY OF THE INVENTION

It has now been found that certain of the foregoing and related objects of the present invention are attained by the provision of a prosthetic dental device comprising a metal core, including a body portion and an integrally formed, projecting neck portion. A first, directly applied layer of a synthetic polymer substantially covers at least the neck portion of the core and is firmly bonded to it. A second such layer covers the first, and a mass of biopolymer fibrils is secured by the second layer; the fibrils project generally outwardly to provide a napped surface substantially covering the polymer-coated portion of the device.

In certain preferred embodiments, the napped surface will substantially cover the entire core, and in other cases only a neck portion will be covered. The core will desirably be fabricated from a nickel/chrome or titanium alloy, and normally the surface to be coated will be roughened, such as by acid etching. The synthetic polymer of both of the applied layers will desirably be a methacrylate polymer or copolymer, applied in monomeric or oligomeric form (hereinafter sometimes referred to as a "polymerizable composition") and polymerized in situ, with the monomer units of the composition which provides the first layer being substantially (typically 90 to 99 percent) polymerized at the time that the polymerizable composition for the second layer is applied. Generally, the biopolymer of which the fibrils are composed will be collagen, fibronectin, collagen-mucopolysaccharide composites, collagen-fibronectin composites, collagen-fibronectin-mucopolysaccharide composites, or keratin; the mucopolysaccharide of such composites will typically be chondroitin 4-sulfate, chondroitin 6-sulfate, dermatan sulfate, keratin sulfate, heparan sulfate, heparin, or hyaluronic acid.

Other objects of the invention are attained by the provision of a method for the production of the prosthetic dental device described. In accordance with the method, a polymerizable composition is applied directly to the surface of at least the neck portion of the metal core component, and is polymerized to produce a first, firmly bonded layer of a synthetic polymer substantially covering it. A coating of a polymerizable composition is then applied to substantially cover the first layer, and a deposit of biopolymer fibrils is applied so as to substantially cover the second layer and project therefrom. Polymerization of the monomer units of the outer coating is effected to produce a second layer of a synthetic polymer, firmly bonded to the first layer and securing the fibrils, thus providing a napped surface thereover. Preferably, the polymerizable composition used for both of the layers will comprise methacrylate monomer units, and most desirably the polymerizable compositions used will contain a photoinitiator that is responsive to actinic radiation.

Additional objects are attained by the provision of a method for the percutaneous implantation of a prosthetic dental device into a host using, in one embodiment, the substantially completely coated prosthetic device described. An incision is made at the crest of the boney ridge of the host's jaw, following which a slot is cut into the bone. The slot will be dimensioned to passively accept the body portion of the device, so as to avoid substantial damage to, or separation of, the fibrils, and to cause the neck portion of the core component to protrude through the plane of the surface of the bone cortex, with the shoulder element disposed below it. The incision is then closed and, following a healing period, a head component is thereafter attached to the neck portion of the core component, to extend above the surface of the jaw; finally, an external dental prosthesis is permanently affixed on the head component.

In another embodiment of the method of the invention the lower portion of the prosthetic device is in the form of a saddle frame, shaped to seat upon the surface of the underlying bone. For implantation, the device (prepared with a napped surface as described) is surgically introduced between the bone and the periosteum, and is mechanically stabilized, such as by use of temporary dental bridge resin, during healing of the incision.

In yet another embodiment, the prosthetic device may be of cylindrical tubular form, with a reduced diameter neck portion at the top within which a head component can be threadably engaged, and to which the napped area is confined. Implantation stability is enhanced by frictional engagement between the uncoated core portion and the host's jawbone, the site having been prepared by cutting a full thickness envelope flap from the epithelium through the periosteum, and drilling the bone to provide a hole of corresponding diameter.

DETAILED DESCRIPTION OF THE ILLUSTRATED EMBODIMENT

Figure 1:
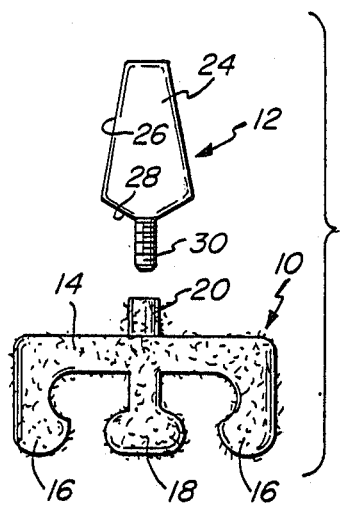
FIG. 1 is an exploded elevational view showing the core and head components constituting a device of the invention.
Figure 2:
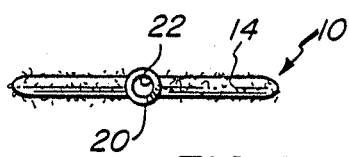
FIG. 2 is a top view showing the core component of the device of FIG. 1.

Turning now in detail to FIGS. 1 and 2 of the appended drawings, therein illustrated is a prosthetic dental device embodying the present invention and consisting of an implantable core component, generally designated by the numeral 10, and a head component generally designated by the numeral 12. The core component is of relatively thin, flat form, and includes an elongated shoulder element 14 from which project, in one direction, three prongs 16, 18, the lower ends of which are bulbously enlarged to increase surface area. A neck portion 20 projects from the shoulder element 14 in the direction opposite to the prongs 16, 18, and it has an inwardly extending threaded bore or socket 22.

The head component 12 consists of a post portion 24, formed with lateral edges 26 which taper at an angle of about 5° to the longitudinal axis of the component, and bottom edges 28 which are disposed at an angle of about 45° thereto. The head component has a stem portion 30, which is threaded to screw into the socket 22 of the core components neck portion 20.

Figure 3:
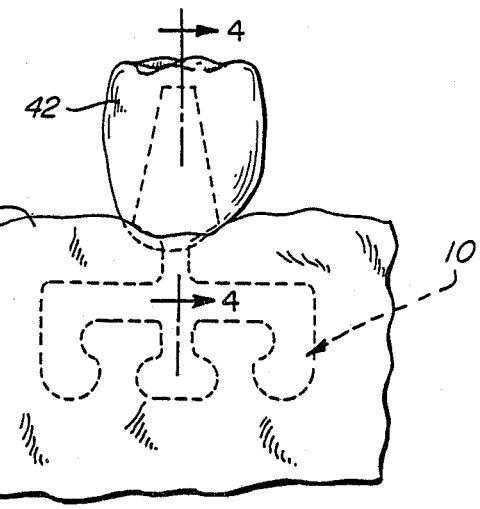
FIG. 3 is an elevational view illustrating the device of FIGS. 1 and 2 implanted within the jawbone of a host, and carrying a dental crown affixed upon the head component thereof.
Figure 4:
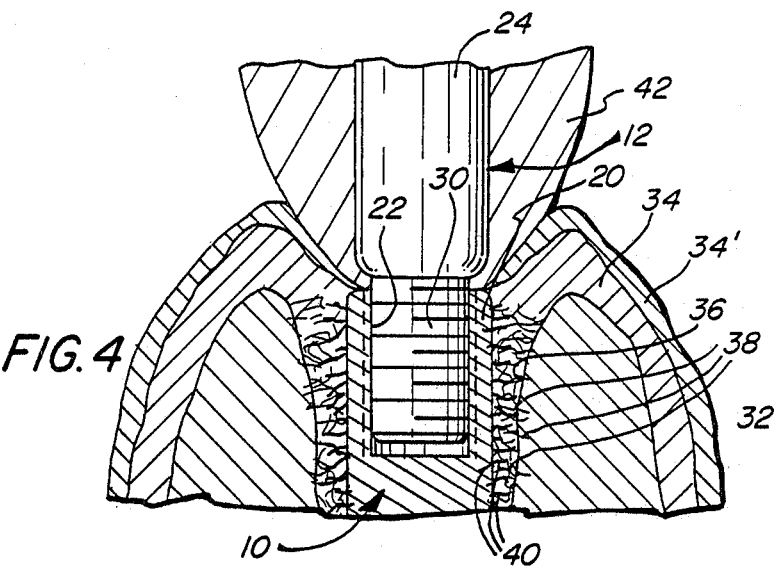
FIG. 4 is a sectional view, taken along line 4—4 of FIG. 3 and drawn to a scale enlarged therefrom, schematically showing the device implanted within the jaw and illustrating the attachment that occurs between the fibrils on the core and regenerated recipient connective tissue.

FIGS. 3 and 4 show the device of the preceding Figures implanted within the jawbone of a host, the bone 32 and gum 34 (with epithelium 34') thereof being schematically illustrated in FIG. 4; a dental crown 42 is affixed to the post 24 of the head component 12. As will be appreciated, preparatory to implantation the gum 34 will have been incised, through the epithelium, submucosa and periosteum, at the crest of the boney ridge of the jaw, and the bone 32 will have been slotted at 36, such as by use as by a surgical burr. It will be noted that the slot 36 is made sufficiently wide and deep to accept the core component 10 with lateral spacing from the bone surfaces, and with the tip of the neck portion 20 protruding only slightly above the plane of the bone cortex.

FIG. 4 also illustrates the connective tissue fibers 38 that have grown from the bone 32, and that are attached to the fibrils 40 constituting the napped surface of the core 10. In the healed state illustrated, the gum of the host has grown to the crown and the surface of the implanted core component 10. It will be noted, however, that the epithelium 34' stops at the top of the core component and that it has not invaded the region downwardly within the jaw bone; this is believed to be a consequence of the inhibiting effect of the fibrils 40 upon such cellular growth.

Figure 5:
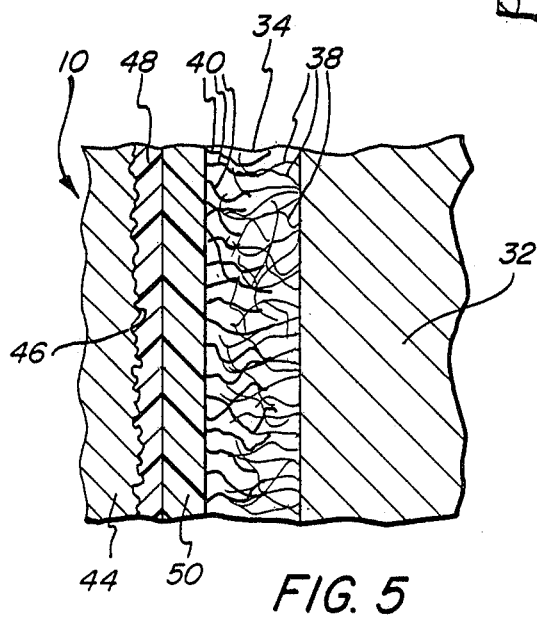
FIG. 5 shows a section of the implant and the adjacent area of the host's jawbone, as depicted in FIG. 4 and drawn to a scale further enlarged therefrom.

The intermingling and mutual bonding that occurs between the regenerative host tissue fibers 38 and the biopolymer fibrils 40 is best illustrated in FIG. 5. It also shows the laminated construction of the core component 10, which consists of the metal substrate 44, a first layer of polymeric material 48 firmly bonded to the etched surface 46 thereof, and a second polymer layer 50 bonded to the layer 48 and anchoring the fibrils 40 of the biopolymer matrix.

Figure 6:
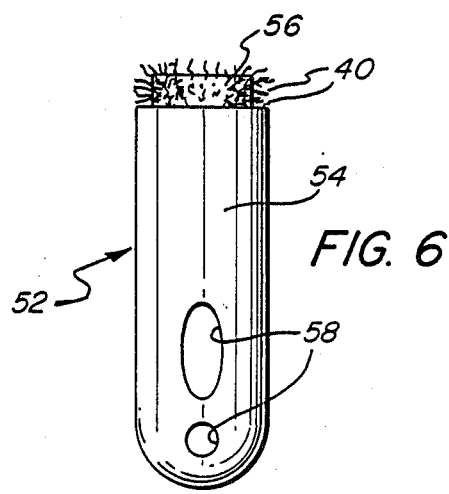
FIG. 6 is an elevational view of a second embodiment of the prosthetic device of the invention.

The implant device of FIG. 6 consists of a cylindrical, tubular core, generally designated by the numeral 52, including a body portion 54 closed at the bottom, and a coaxial neck portion 56 at the top thereof. The core 52 will advantageously be fabricated from a titanium alloy, and will normally be about 8 to 15 millimeters long and 3 to 4 millimeters in diameter; the neck portion 56 will typically be about 2 millimeters long and formed by a circumferential recess or shoulder that is about 0.5 millimeter deep.

Perforations 58 are provided in the body portion 54, to allow bone growth therethrough and thereby to promote secure anchoring of the implant. It will be noted that, in this embodiment, only the neck portion 56 of the core carries a nap of fibrils 40; the implantation technique employed involves drilling of a hole in the patient's jaw bone, which is sized to provide a friction fit with the core, and the body portion 54 is therefore maintained substantially free of fibrils to prevent interference. Nevertheless, the collar element that is formed on the neck portion 56 from the polymer/fibril composite (produced in the manner hereinbefore described) will effectively inhibit epithelial downgrowth, while also providing a site for secure connection of regenerated tissue. The top opening of the core, through the neck portion, will usually be threaded for engagement of a head component 12, also as previously described, and it will be appreciated that only the neck portion need be roughened if it is desired to enhance bond strength in that manner.

As will be apparent to those skilled in the art, the core or body of the implantable device will normally be fabricated from a base metal alloy, e.g., nickel-chrome, chrome-cobalt, molybdenum and titanium alloys. In the embodiment shown in FIGS. 1-3, the core component is advantageously configured to afford secure mechanical interengagement and to provide a relatively large surface area to maximize sites for attachment of regenerative tissue fibers. Although it is formed to provide three prong elements, often a two-pronged form will be more suitable; in any event, the optimal configuration for the subcutaneous, implant frame portion will depend upon a number of evident factors, such as the nature of the exterior prosthesis that it is to support, the position of placement in the jaw, etc. As noted above, it may have a portion of saddle-like character, to seat upon the bone rather than being inserted into it. Although adhesion of the synthetic resinous base layer will normally be promoted by acid etching of the underlying metal, similar roughening of the surface can be produced by other techniques as well, such as by sandblasting.

The tapered edges shown on the illustrated head component of the implant assembly are provided to facilitate cleaning, and also to promote the formation of a tight seal with the crown or other prosthesis applied. Generally, the head component will be made of the same alloy as the core component. Both can often be produced simultaneously, by use of conventional investment casting dental techniques, followed by drilling and tapping to produce the desired threaded elements for joining them. After cleaning (e.g., in hydrochloric acid), rinsing and drying, the core component may conveniently be mounted upon a handle having a threaded stem, to facilitate application of the polymer layers and the fibril nap.

Although a wide variety of synthetic resinous materials may be employed for the two polymer layers applied to the metal substrate, acrylate and methacrylate polymers and copolymers will generally be preferred; the polyurethanes and the polystyrene resins constitute additional classes of suitable polymers, and it will be appreciated that the same resin need not be employed for both layers. The polymer used will normally be unfilled, although appropriate agents, such as antibiotics to minimize any possibility of infection, may be incorporated if so desired.

Application of the first layer may be achieved by brushing a liquid polymerizable composition, desirably containing a photoinitiator, upon the metal surface so as to provide complete coverage with no gaps or pinholes; generally, a coating about 0.2 millimeter thick will suffice. Utilizing, for example, the bis-glycidyl methacrylate product sold by L. D. Caulk, of Milford, Del., under the trade designation "PRISMA BOND", exposure to direct visible light for a period of 20 seconds will produce the desired degree of polymerization; i.e., about 90 to 99 percent of the reactive monomeric units will be converted. Thereafter, a second coating of the same polymerizable composition may be applied to the substantially polymerized first layer, followed by application of the fibrils.

A nap of collagen (native or cross-linked) fibrils has been found (as mentioned above) to inhibit epithelial advance, and is therefore presently regarded to constitute the best mode for practicing the invention. It is believed, however, that fibronectin may also provide especially desirable results; fibrils of other biopolymeric compositions, suitable for use herein, have been indicated hereinabove as well, and yet additional materials may occur to those skilled in the art. Following application of the fibrils (which may be achieved simply by dipping the uncured prepolymer-coated body into a bed of the dry material), polymerization of the monomeric units of the polymerizable outer coating is initiated, again by exposure to the actinic source, and after a period of about 40 seconds the device will normally be ready for surgical implantation. Perhaps it should be emphasized that reference herein to "monomeric units" is intended to encompass any monomer, oligomer or other species of the polymerizable composition that is capable of polymerization.

As indicated above, one technique for implantation involves the cutting of a slot into the bone of the jaw, which will be made sufficiently wide and deep to accept the implant passively; i.e., with sufficient spacing between the bone surfaces defining the sides of the slot and the core component to avoid rubbing and abrasion, as is important to minimize fibril damage and disengagement from the anchoring polymer matrix, when the inserted portion is provided with a napped surface. The neck of the core component must of course extend slightly above the natural gum surface, not only to enable testing during the healing procedure (to ensure that the implant has been firmly set and is stable and immobile), but also to enable ready assembly of the head component preliminary to application of the crown, pontic or other dental prosthesis.

Thus, it can be seen that the present invention provides a biologically compatible, implantable dental device which enables the formation of a physiological bond between the implant and host tissue, by virtue of a fibroblastic/fibrocytic response, and which affords inherent mechanical strength and rigidity, nontoxicity and low immunogenicity. The anchored biopolymer fibrils serve to promote connective tissue healing and secure bonding of the implant to the connective tissue; furthermore, they inhibit epithelial invasion, thereby deterring implant rejection. Thus, a novel implantable percutaneous device is provided, which is highly effective in providing a support for an external dental prosthesis and in avoiding immunological rejection due to epidermal downgrowth. Novel methods for producing such a device, and for carrying out the surgical implantation thereof, are also provided.

Having thus described the invention, what is claimed is:

1. A prosthetic dental device for percutaneous implantation, comprising a metal core component including a body portion, elongated in the direction of a first axis, and an integrally formed neck portion projecting therefrom along said first axis, said neck portion having a lateral surface extending thereabout and for a substantial distance therealong in the direction of said first axis; a thin first layer of a synthetic polymer substantially covering at least said lateral surface of said neck portion of said component, said first layer being applied directly to said metal and being firmly bonded thereto; a thin second layer of a synthetic polymer substantially covering said first layer, said second layer being applied directly to said first layer and being firmly bonded thereto; and a mass of biopolymer fibrils embedded in and secured by said second layer and projecting therefrom, said fibrils substantially covering at least said lateral surface of said neck portion of said core component and providing a napped surface thereover; said body portion of said core component having a surface character affording firm setting, immobility, rigidity and stability of the device when implanted.

2. The device of claim 1 wherein said neck portion is threaded and is adapted to receive a head component having a matingly threaded element thereon, said device additionally including a head component having a projecting threaded stem element adapted to threadably engage said neck portion of said core.

3. The device of claim 1 wherein said synthetic polymer of both of said first and second layers is a methacrylate polymer or copolymer applied as a polymerizable composition and polymerized in situ, the monomer units of said polymerizable composition of said first layer being substantially, but not completely, polymerized at the time that the monomer units of said polymerizable composition of said second layer is applied thereto.

4. The device of claim 1 wherein the biopolymer of which said fibrils are composed is selected from the group consisting of collagen, fibronectin, collagen-mucopolysaccharide composites, collagen-fibronectin composites, collagen-fibronectin-mucopolysaccharide composites, and keratin, the mucopolysaccharide of said composites being selected from the class consisting of chondroitin 4-sulfate, chondroitin 6-sulfate, dermatan sulfate, keratin sulfate, heparan sulfate, heparin, and hyaluronic acid.

5. The device of claim 1 wherein said first and second layers, and said mass of fibrils, substantially cover the entire exposed surface of said core component.

6. The device of claim 5 wherein said body portion comprises an elongated shoulder element and a plurality of prong elements extending in substantially the same direction therefrom, said neck portion extending oppositely to said prong elements from said shoulder element, said body portion being of relatively thin, flat construction.

7. The device of claim 5 wherein said core is fabricated from a nickel/chrome alloy, and has a surface roughened by acid etching.

8. The device of claim 1 wherein said body portion is of tubular, cylindrical form and is coaxial with said neck portion, and wherein said body portion is substantially free of said first and second layers and said fibrils.

9. The device of claim 8 wherein said core is fabricated from a titanium alloy, and wherein at least said neck portion thereof has a roughened surface.

10. A method for the production of a prosthetic dental device for percutaneous implantation, comprising the steps:

providing a metal core component including a body portion, elongated in the direction of a first axis, and an integrally formed neck portion projecting therefrom along said first axis, said neck portion having a lateral surface extending thereabout and for a substantial distance therealong in the direction of said first axis, at least said neck portion of said core component having a roughened surface character;

applying directly to the metal of at least said lateral surface of said neck portion of said component a polymerizable composition that is capable of polymerization to produce a firm bond therewith, to substantially coat the same;

effecting polymerization of the monomer units of said composition to produce a thin first layer of a synthetic polymer substantially covering at least said lateral surface of said neck portion of said component and firmly bonded thereto;

applying directly to said first layer a polymerizable composition that is capable of polymerization to produce a firm bond therewith, to substantially coat the same and to provide an outer coating of polymerizable composition;

applying to said outer coating a deposit a biopolymer fibrils, the amount of said deposit and the thickness of said outer coating being such as to cause said fibrils to substantially cover at least said neck portion of said core component and to project from said outer coating; and effecting polymerization of the monomer units of said composition of said outer coating to product a thin second layer of a synthetic polymer firmly bonded to said first layer and securing said fibrils thereto, said fibrils substantially covering at least said neck portion of said core component and providing as napped surface thereover; said body portion of said core component having a surface character affording firm setting, immobility, rigidity and stability of the device when implanted.

11. The method of claim 10 including the additional step of treating the surface of said metal core with acid to effect etching, and thereby roughening, thereof.

12. The method of claim 10 wherein said first and second layers are comprised of methacrylate polymer, and wherein said step of effecting polymerization of said polymerizable composition first applied is carried out to effect substantial, but not complete, polymerization of the monomer units thereof at the time that said polymerizable composition of said outer coating is applied thereto.

13. The method of claim 12 wherein, at the time said polymerizable composition of said outer coating is applied, said monomer units of said polymerizable composition first applied are about 90 to 99 percent polymerized.

14. The method of claim 10 wherein said polymerizable composition for both of said layers comprises a formulation containing a photoinitiator, and wherein said steps of effecting polymerization are initiated by exposing said composition to actinic radiation to which said photoinitiator is responsive.

15. The method of claim 10 wherein the biopolymer of which said fibrils are composed is selected from the group consisting of collagen, fibronectin, collagen-mucopolysaccharide composites, collagen-fibronectin composites, collagen-fibronectin-mucopolysaccharide composites, and keratin, the mucopolysaccharide of said composites being selected from the class consisting of chondroitin 4-sulfate, chondroitin 6-sulfate, dermatan sulfate, keratin sulfate, heparan sulfate, heparin, and hyaluronic acid.

16. A prosthetic dental device for percutaneous implantation, comprising:
  a metal core component including a body portion of thin, flat construction, and an integrally formed neck portion projecting therefrom, said body portion comprising an elongated shoulder element and a plurality of prong elements, said prong elements extending in the direction of a first axis from said shoulder element and having bulbously enlarged free outer end portions thereon, said neck portion extending oppositely to said prong elements from said should element along said first axis, said neck portion having a lateral surface extending thereabout and for substantial distance therealong in the direction of said first axis; a first thin layer of a synthetic polymer substantially covering said core component, said first layer being applied directly to said metal and being firmly bonded thereto; a second thin layer of a synthetic polymer substantially covering said first layer, and a second layer being applied directly to said first layer and being firmly bonded thereto; and a mass of bipolymer fibrils embedded in and secured by said second layer and projecting therefrom, said fibrils substantially covering the entire exposed surface of said core component and providing a napped surface thereover, said first and second layer and said fibrils enabling firm setting, immobility, rigidity and stability of the device when implanted; and
  a metal head component having a projecting stem element, said stem element and said neck portion being threaded for interengagement to mount said head component on said core component.

17. A prosthetic dental device for percutaneous implantation, comprising:
  a metal core component including a tubular, cylindrical body portion and an integrally formed, reduced-diameter neck portion projecting coaxially from one end thereof, said neck portion having a lateral surface extending thereabout and for a substantial distance in the direction of the axis of said core component; a thin first layer of a synthetic polymer substantially covering said lateral surface of said neck portion of core component, said first layer being applied directly to said metal and being firmly bonded thereto; a thin second layer of a synthetic polymer substantially covering said first layer, said second layer being applied directly to said first layer and being firmly bonded thereto; and a mass of biopolymer fibrils embedded in and secured by said second layer and projecting therefrom, said fibrils substantially covering said lateral surface of said neck portion of said core component and providing a napped surface thereover, said body portion of said core component being substantially free from said layers and said fibrils, with the metal thereof providing the exposed surface to enable firm setting, immobility, rigidity and stability of the device when implanted; and
  a metal head component having a projecting stem element, said stem element and said neck portion being threaded for interengagement to mount said head component on said core component.

18. In a method for the percutaneous implantation of a prosthetic dental device into a host mammal, the steps comprising:
  providing a prosthetic dental device comprising: a metal core component including a body portion, elongated in the direction of a first axis, and an integrally formed neck portion projecting therefrom along said first axis, said neck portion having a lateral surface extending thereabout and for a substantial distance therealong in the direction of said first axis; a thin first layer of a synthetic polymer substantially covering at least said lateral surface of said neck portion of said component, said first layer being applied directly to said metal and being firmly bonded thereto; a thin second layer of a synthetic polymer substantially covering said first layer, said second layer being applied directly to said first layer and being firmly bonded thereto; and a mass of biopolymer fibrils embedded in and secured by said second layer and projecting therefrom, said fibrils substantially covering at least said lateral surface of said neck portion of said core component and providing a napped surface thereover; said body portion of said core component having a surface character affording firm setting, immobility, rigidity and stability of the device when implanted;
  making an incision at the crest of the bony ridge of the jaw, and to the jawbone, of the host mammal;
  inserting said core component into said incision to bring said body portion into engagement with said jawbone, with said neck portion adjacent the plane of the surface of the bony cortex of said jaw, and with said metal of said core portion, or said fibrils thereon, in direct contact with said jawbone;
  closing said incision;
  providing a period for healing of said incision;
  providing a head component, and attaching said head component to said neck portion, following said period for healing, to project above said surface of said jaw; and
  providing an external dental prosthesis, and permanently affixing said prosthesis upon said head component.

19. The method of claim 18 wherein said core component is substantially completely coated with said fibrils to provide said napped surface thereover, and wherein said method includes the additional step of cutting into said jawbone a slot dimensioned to passively accept said body portion of said core component of said device, so as to avoid substantial damage to, or disengagement of, said fibrils thereon, and with said neck portion protruding through said plane of the surface of the bone cortex and with said shoulder element therebelow.

20. The method of claim 18 wherein said period for healing is a period of about six months' duration.

* * * * *

UNITED STATES PATENT AND TRADEMARK OFFICE
CERTIFICATE OF CORRECTION

PATENT NO. : 4,812,120

DATED : March 14, 1989

INVENTOR(S) : Dennis F. Flanagan; Stephen H. Clark

It is certified that error appears in the above-identified patent and that said Letters Patent is hereby corrected as shown below:

Column 9, line 35, insert after the word "for" the word --a--; same column, line 48, delete the word "layer" and substitute therefor --layers--.

First page, add the following under "U.S. Patent Documents":
```
--3,556,969    1/1971    Mizuguchi et al    204/181.4
  3,700,609   10/1972    Tregear et al      521/53
  3,808,113    4/1974    Okamura et al      427/44
  3,863,344    2/1975    Pillet             128/155
  4,034,750    7/1977    Seiderman          128/156
  4,060,081   11/1977    Yannis et al       623/11
  4,307,472   12/1981    Morris             128/Dig.8
  4,427,808              Stole et al        623/18
  4,491,987    1/1985    Park
```

Same page, insert:
--OTHER PUBLICATIONS
  Dialog publication of Kantrovitz et al. Appln. Serial No. 615,883
  "Contemporary Biomaterials" (Noyes Publications, Park Ridge, New Jersey 1984) beginning at page 506--

Signed and Sealed this

Seventeenth Day of April, 1990

Attest:

HARRY F. MANBECK, JR.

*Attesting Officer*              *Commissioner of Patents and Trademarks*